United States Patent [19]
Dahill, Jr.

[11] 3,962,354
[45] June 8, 1976

[54] SYNTHESIS OF CIS-3-HEXEN-1-OL

[75] Inventor: Robert T. Dahill, Jr., Perth Amboy, N.J.

[73] Assignee: Givaudan Corporation, Clifton, N.J.

[22] Filed: Jan. 14, 1975

[21] Appl. No.: 540,940

Related U.S. Application Data

[63] Continuation of Ser. No. 49,544, June 24, 1970, abandoned.

[52] U.S. Cl. .......................... 260/638 R; 204/59 R; 252/522; 260/456 R; 260/456 P; 260/483; 260/484 R; 260/611 R; 260/611 A; 260/612 D; 426/650
[51] Int. Cl.² ......................................... C07C 29/00
[58] Field of Search ..................... 260/632 R, 638 R

[56] References Cited
UNITED STATES PATENTS

| | | | |
|---|---|---|---|
| 2,493,038 | 1/1950 | Snyder et al. | 260/632 R |
| 3,579,550 | 5/1971 | Demole | 260/638 A |

*Primary Examiner*—Joseph E. Evans
*Attorney, Agent, or Firm*—Thomas Cifelli, Jr.

[57] ABSTRACT

There is provided a novel method of preparing the highly desired odorant cis-3-hexen-1-ol from alkyl phenyl ethers. The method comprises Birch reduction of the alkyl phenyl ether, sequentially followed by oxidative ring cleavage and reduction.

5 Claims, No Drawings

SYNTHESIS OF CIS-3-HEXEN-1-OL

This is a continuation of application Ser. No. 49,544 filed June 24, 1970 now abandoned.

DESCRIPTION OF THE PRIOR ART

Cis 3-hexen-1-ol is a naturally occuring alcohol present in mulberry tree leaves, radish leaves, acaccia leaves and other plants.

It has been produced synthetically by an acetylenic route by Bedoukian (Am. Perf. and Cos 78, 31 (1963).

This route, while practical is subject to the handling problems known to affect industrial scale acetylenic route synthesis.

SUMMARY OF THE INVENTION

In the process of the present reaction on alkyl phenyl ether (I) is subjected to 1,4-ring reduction suitably by the action of an alkali metal solvated in an amine together with a proton source, for example, by means of the Birch reduction. The 1,2-double bond is cleaved by selective oxidation, suitably by ozonolysis to yield the aldehyde ester (III) which is not isolated but is reduced to the alcohol (IV) esterification of the alcohol (IV) with a sulfonyl halide followed by further reduction yields the desired alcohol (VI).

The reaction sequence is illustrated as follows:

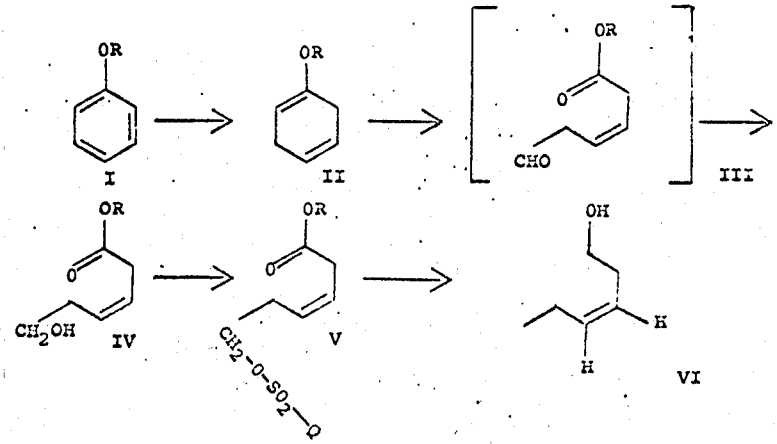

wherein R is lower alkyl of 1–6 carbons or lower cycloalkyl of 4–8 carbons.

And Q is alkyl, of 1–6 carbons, aryl for example phenyl, tolyl, or napthyl where the alkyl group has 1–6 carbons and the aryl group is, for example phenyl or napthyl.

Alternatively, where R is phenyl, the reaction procedes in an analogous manner.

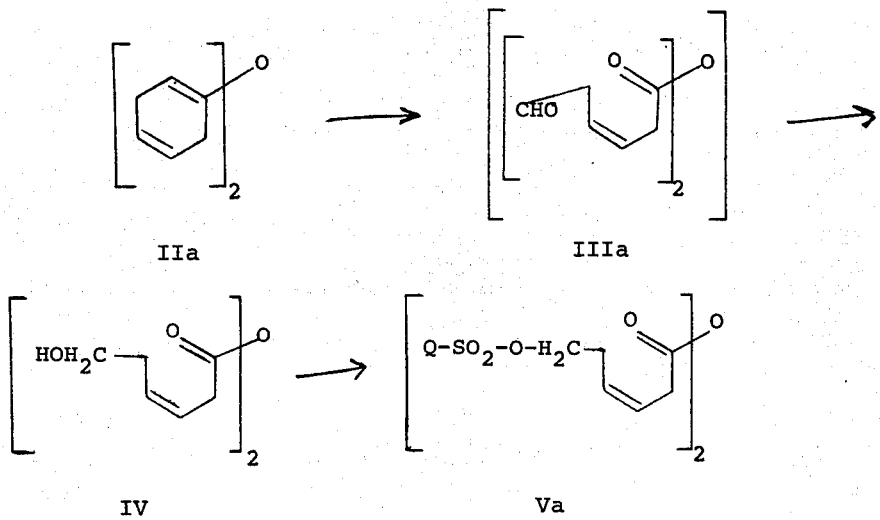

DESCRIPTION OF THE PREFERRED EMBODIMENTS

The alkyl phenyl ethers of formula (I) are well known in the art.

In the Birch reduction there is prepared a solution of the compound I to be reduced, suitably in dry ether and the ethereal solution added to liquid ammonia. Alkali metal, suitably sodium, potassium or lithium is added thereto. The mixture is allowed to stand, suitably with agitation until all of the metal has dissolved. An alkanol, suitably ethanol is added until the blue color disappears and the ammonia permitted to evaporate at ambient temperature. Water is added and the reaction worked up in the usual manner.

In place of using ammonia as the solvent, an alkyl amine may be used. Ether may be used. It is preferred however to operate in liquid ammonia due to the relative ease of obtaining a solution of alkali metals.

In yet another modification the Birch reduction may be performed electrolytically by passing direct current through a solution of the aromatic ether, lithium chloride and methyl amine. While this method is not the method of choice in small scale synthesis, the elimination of the cooling and condensation facilities required for liquid-ammonia may make it the method of choice for industrial synthesis.

In the liquid ammonia modification there are utilized from about 10 to about 20 volumes of liquid ammonia to each part by weight of aryl ether. There is employed an excess of alkali metal, suitably 4.5 moles of metal/mole of aryl ether.

In the electrolytic method one can use 8 moles of lithium chloride and 30 moles of methyl amine per mole of aryl ether.

A current density of 0.2 amps/cm$^2$ at 85 volts.

The temperature is maintained at the boiling point of the amine.

The enol ether (i.e., 1,2-) is then oxidatively cleaved, cleavage may be accomplished by epoxidation, conversion to glycol and oxidation with periodic acid, permanganate oxidation, or ozonlysis; preferred among these methods however is ozonolysis.

In this modification the diene (II) is taken up in a suitable solvent, preferably an alkanol such as methanol and cooled to dry ice temperature (ca-78°C).

An equimolar amount of ozone is then introduced in the usual manner at this temperature. The excess ozone is then flushed out with an inert gas and the mixture permitted to warm up to about 0°C.

The ozonide is then decomposed and subsequently, (in situ) reduced to the corresponding alcohol ester (IV). Among the suitable reducing agents may be mentioned dimethyl sulfide, sodium iodide, potassium iodide, zinc or magnesium in the presence of acetic acid or water, sulfur dioxide or sources thereof such as sodium bisulfite, stannous chloride, formaldehyde and inorganic or organic phosphites or similar mild reducing agents known to the art.

Raney nickel may also be employed, as may catalytic hydrogenation. This last is not favored due to the control required to ensure that reduction does not proceed too far.

Of these reducing agents dimethyl sulfide is preferred. There is added a slight excess of this reagent, from 1 to 2 moles of sulfide per mol of ozonide, suitably about 1.5 moles of sulfide per mole being preferred.

Without further work-up the reaction mixture containing the aldehyde ester (III) is reduced to the corresponding alcohol. In the preferred method there is added a slight excess of sodium borohydride in an alkanol, suitably in absolute ethanol. These are utilized between 1 and 2, suitably about 1.5 moles of sodium borohydride per mole of originally charged alkyl cyclohexadienyl ether (II).

The addition is carried out at dry ice temperatures (ca-78°C). After addition of the reducing agent the reaction mixture is allowed to warm to ambient temperatures and stirred for from about 1 to about 2 hours.

The solvents are then removed, suitably by distillation under reduced pressure to yield the hydroxy ester (IV), which may be further purified by distillation.

The hydroxy ester (IV) is then reduced to the desired hexenylalcohol (IV). In this step the hydroxy group of ester (IV) is sulfonated, suitably by reaction with a sulfonyl halide suitably an alkyl, aryl, or alkaryl sulfonyl halide, such as toluene sulfonyl chloride, methane sulfonyl chloride and the like in the usual manner by mixing the reactants at moderately low temperatures, say about 0°C in a weak organic base such as triethylamine or pyridine, followed by acidification and extraction of the product by a water immiscible solvent.

The ester sulfonate (V) is then reduced to the desired hexenol (VI). Among the preferred reducing agents are: lithium aluminum hydride and lithium in liq. NH$_3$. Especially preferred is lithium aluminum hydride. The ester sulfonate (V) is taken up in a suitable solvent, such as benzene, tetrahydrofuran or diethyl ether to which is added an excess of lithium aluminum hydride in a similar solvent. There are utilized from about 1 to about 2 moles of reducing agent per mole of sulfonate (V) suitably about 1.8 moles of the hydride are used.

Addition is carried out at between about 15°C and about 30°C, suitably at about 25°C. After completion of addition the reaction mixture is stirred for about 1 hour, and is quenched, suitably by addition of wet ether, ethyl acetate or water.

Work-up in the usual manner yields the desired alcohol (VI).

The cis 3-hexen-1-ol is used in perfume and fragrance compositions (see M. Barnard, Parfumerie, Cosmetique, Savons 5, 105 (1962).

EXAMPLE I

1-Methoxy-1, 4-cyclohexadiene

A solution of 150 g. of anisole in 500 ml. of dry ether and 2 liters of liquid ammonia which was distilled from sodium was placed in a 5 l. three necked flask fitted with a mechanical agitator, dry ice condenser and dropping funnel and cooled with a dry ice-ethyl alcohol bath. To this mixture was added 45 g. of lithium wire in small pieces. After the addition was complete, absolute ethyl alcohol (about 1250 ml.) was added until the blue color disappeared. The resulting mixture was left in a good exhaust hood for the ammonia to evaporate. Water (500 ml.) was cautiously added to the resulting mixture and the precipitate filtered off. The organic layer was separated and the water layer extracted three times with 100 ml. of ether. The combined organic solutions were washed neutral with water and dried over anhydrous potassium carbonate. The solvent was removed by atmospheric distillation through a 37 cm. column packed with glass helices. There was produced 132.4 g. (86.5% of theory). This material analyzed as 92.5% 1-methoxy-1,4-cyclohexadiene and 7.5% 1-methoxy-1,3-cyclohexadiene. B.P. 75°–80°C (11 mm.).

I.R. 5.90$\mu$, 6.05$\mu$ (olefin), 8.20$\mu$ (enol ether).
N.M.R. 4.30$\gamma$(2H, multiplet, olefinic protons),
5.35$\gamma$(1H, broad, olefinic protons),
6.48$\gamma$(3H, singlet, —OCH$_3$),
7.25$\gamma\gamma$(4H, multiplet, —CH$_2$—)

EXAMPLE II

Methyl cis 6-hydroxy-3-hexenoate

A mixture of 2.85 g. (26 mmoles)of 1-methoxy-1, 4-cyclohexadiene and 30 ml. of absolute methanol was treated with ozone (1.25 g., 26 mmoles) at −78°C. The resulting mixture was flushed with nitrogen. The mixture was allowed to come to 0°C and 2.42 g. (39 mmoles) of dimethylsulfide were added and the mixture stirred at this temperature for 80 minutes. After cooling to −78°C, a suspension of 1.47 g/ (39 mmoles) of sodium borohydride in 20 ml. of absolute ethanol was added dropwise. The resulting mixture was allowed to come up to room temperature and then stirred for 80 minutes. The methanol was removed under vacuum to produce 3.3 g. of product (88% of theory). B.p. 60° (0.2 mm., short path distillation).

I.R. 2.90$\mu$ (—OH), 5.74$\mu$ (C=O).
N.M.R. 4.32$\gamma$ (2H, multiplet, olefinic), 6.30γγ(3H, singlet, —OC$\underline{H}$3),
6.32γ(2H, J=7, triplet, —C$\underline{H}_2$—OH),
6.84γ (2H, doublet, J=8, —$\underline{C}H_2$—CO—),
7.48γ (broad, —O$\underline{H}$),
7.66γ(2H, multiplet, HOC$\underline{H}_2$—CH2—CH = CH).

EXAMPLE III

Methyl cis 6-hydroxy-3-hexenoate p-toluene sulfonate p-Toluene sulfonyl chloride (1.425 g., 7.5 mm.) was added at 0°C to a solution of 1.00g. (6.95 mm.) of methyl cis 6-hydroxy-3-hexenoate in 2.37 g. of dry pyridine. The resulting mixture was stirred at 0°C for 4 hours. The crude product was poured on ice and concentrated hydrochloric acid, extracted with benzene, washed with 2N hydrochloric acid, sodium carbonate till neutral and dried over potassium carbonate. Evaporation of the solvent produced 1.425 g. (68% of theory) of crude tosylate.

I.R. 5.80μ ( C=O), 6.25μ and 6.98μ (>C = C<).
N.M.R. 2.65γ (4H, multiplet, aromatic),
4.40γ (2H, multiplet, olefinic),
5.93γ (2H, triplet, J=7, —C$\underline{H}_2$—O),
6.31γ (3H, singlet, —OCH$_3$).
6.94γ (2H, doublet, J=8, —C$\underline{H}_2$—C—),
7.56γ (3H, singlet, —CH3),
7.62γ (2H, multiplet, —CH$_2$—CH= ).

EXAMPLE IV

Cis 3-hexen-1-ol

Crude methyl cis 6-hydroxy-3-hexenoate p-toluene sulfonate (1.357 g., 4.85 mm.) was dissolved in 20 ml. of dry ether. To this solution was added 0.342 g. (9.00 mm.) of lithium aluminum hydride in 20 ml. of dry ether at 25° with stirring. After the addition was completed the mixture was stirred at 25° for 1 hour. The excess lithium aluminum hydride was decomposed by the addition of first wet ether and finally water. The product was extracted with ether and dried over sodium sulfate. After the ether was evaporated the product was distilled through a short path distillation apparatus to give 0.358 g. (3.58 mm., 74% of theory) of Cis 3-hexen-1-ol, b.p. 70° (27 mm.).

I.R. 3.00μ (—OH), 13.80μ

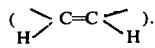

N.M.R. 4.54γ (2H, multiplet, olefinic protons),
6.37γ (2H, triplet, J=7, —CH$_2$—O—),
7.68γ and 7.92γ (4H, quartets, J=7, methylenes α to double bonds).

All of the spectral data as well as the vapor phase chromatogram of this material was identical with that of an authentic sample prepared via the traditional acetylenic approach.

EXAMPLE V

1-Ethoxy-1, 4-cyclohexadiene

A solution of 59.5 g. of phenetole (ethyl phenyl ether) in 200 ml. of dry ether and 800 ml. of liquid ammonia which was distilled from sodium was placed in a 2 l. three necked flask fitted with a mechanical agitator, dry ice condenser and dropping funnel and cooled with a dry ice - ethyl alcohol bath. To this mixture was added 14.1 g. of lithium wire in small pieces. After the addition was complete, absolute ethyl alcohol (about 400 ml.) was added until the blue color disappeared. The resulting mixture was left in a good exhaust hood for the ammonia to evaporate. Water (200 ml.) was cautiously added to the resulting mixture and the precipitate filtered off. The organic layer was separated and the water layer extracted three times with 50 ml. of ether. The combined organic solutions were washed neutral with water and dried over anhydrous potassium carbonate. The solvent was removed by atmospheric distillation through a 37 cm. column packed with glass helices. There was produced 45 g. (75% of theory). This material analyzed as 86% 1-ethoxy-1,3-cyclohexadiene.

I.R. 5.90 μ,6.05μ(olefinic) , 8.30μ(enol ether). μ
N.M.R. 4.35 γ (2H, multiplet, olefinic protons),
5.40 γ (1H, broad, olefinic proton),
6.35 γ (2H, quartet, J=7, —O—C$\underline{H}$2—)
7.27 γ (4H, multiplet, —CH2—),
8.75 γ (3H, triplet, J=7, —C$\underline{H}$3).

EXAMPLE VI

Ethyl cis 6-hydroxy-3-hexenoate

A mixture of 6.30 g. (50 mmoles) of 1-ethoxy-1, 4-cyclohexadiene and 100 ml. of absolute methanol was treated with ozone (2.40 g., 50 mmoles) at −78°C. The resulting mixture was flushed with nitrogen. The mixture was allowed to come to 0°C. and 4.84 g. (78 mmoles) of dimethylsulfide were added and the mixture stirred at this temperature for 80 minutes. The alcohol was removed under vacuum to produce 5.1 g. (32.3 mmole, 65% of theory) of ethyl cis 6 hydroxy-3 hexenoate, b.p. 70° (0.3 mm., short path distillation).

I.R. 2.90 μ (—OH), 5.76μ(C=O).
N.M.R. 4.42 γ (2H, multiplet, olefinic),
5.92 γ (2H, quartet, J=8, —O—C$\underline{H}_2$—CH3),
6.37 γ (2H, J=7, triplet, —C$\underline{H}$2—OH),
6.95 γ (2H, J=6, doublet, —C$\underline{H}_2$—C=O),
7.70 γ (3H, multiplet, —C$\underline{H}_2$— and —O$\underline{H}$),
8.75 γ (3H, triplet, J=8, O—CH$_2$—C$\underline{H}_3$).

EXAMPLE VII

Ethyl cis 6-hydroxy-3-hexenoate p-toluene sulfonate p-Toluene sulfonyl chloride (1.425 g., 7.5mm.) was added at 0°C to a solution of 1.00 g. (6.3mm.) of ethyl cis 6-hydroxy-3,hexenoate in 10 g. of dry pyridine. The resulting mixture was stirred at 0°C for 4 hours. The crude product was poured on ice and concentrated hydrochloric acid, extracted with benzene, washed with 2N hydrochloric acid, sodium carbonate till neutral and dried over potassium carbonate. Evaporation of the solvent produced 1.42 g. (4.85 mm., 77% of theory) of product homogeneous at 225°C. on a 20 M vpc column.

I.R. 5.80μ(C=O); 6.25μ and 6.98μ ( C=C ).
N.M.R. 2.67γ(4H, multiplet aromatic),
4.40γ(2H, multiplet, olefinic),
5.96γ(4H, multiplet, -C$\underline{H}_2$—O—),
6.94γ(2H, doublet, J=8,

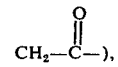

7.55γ(3H, singlet, —C$\underline{H}_3$),
7.65γ2H, miltiplet, —$\underline{C}$H$_2$—CH=),
8.66γ3H, triplet, J=8, C$\underline{H}_3$—CH$_2$—).

EXAMPLE VIII cis 3-Hexen-1-ol

Crude ethyl cis 6-hydroxy-3-hexenoate p-toluene sulfonate (1.43 g., 4.85 mm.) was dissolved in 20 ml. of dry ether. To this solution was added 342 mg. (9.00 mm.) of lithium aluminum hydride in dry ether. After the addition was complete the mixture was stirred at 25°C. for 1 hour. The excess lithium aluminum hydride was decomposed with first wet either and finally water. The product was extracted with ether, dried over magnesium sulfate and the solvent evaporated. There was produced 0.4 g. (4 mm.) of cis-3-hexen-1-ol (82.5% of theory). VPC was identical with authentic sample.

EXAMPLE IX

1-Isopropoxy-1,4-cyclohexadiene

A solution of 65 g. of isopropyl phenyl ether in 250 ml. of dry ether and 1 liter of liquid ammonia which was distilled from sodium was placed in a 3 liter necked flask fitted with a mechanical agitator, dry ice condenser and dropping funnel and cooled with a dry ice-ethyl alcohol bath. To this mixture was added 16.6 g. of lithium in small pieces. After the addition was complete, absolute ethyl alcohol (about 460 ml.) was added until the blue color disappeared. The resulting mixture was left in a good exhaust hood for the ammonia to evaporate. Water (200 ml.) was cautiously added to the resulting mixture and the precipitate filtered off. The organic layer separated and the water layer extracted three times with 100 ml. of ether. The combined organic solutions were washed neutral with water and dried over anhydrous potassium carbonate. The solvent was removed by atmospheric distillation through a 37 cm. column packed with glass helices. There was produced 44.5 g. (68% of theory) of 1-isopropoxy-1,4-cyclohexadiene b.p. 61° –5° (8 mm.).

I.R. 5.95 μ 6.10 (olefin), 8.12μ(enol ether).
N.M.R.4.30 μ (2H, multiplet, olefinic protons),
5.35 γ (1H, broad, olefinic proton),
5.75 γ (1H, heptet, —C$\underline{H}$ (CH$_3$)$_2$, J = 6),
7.28 γ (4H, multiplet, —CH—$_2$),
8.80 γ (6H, doublet, —CH(C$\underline{H}_3$)$_2$, J = 6).

EXAMPLE X

Isopropyl cis-6-hydroxy-3-hexenoate

A mixture of 3.60 g. (26 mm.) of 1-isopropoxy-1,4-cyclohexadiene and 100 ml. of absolute methanol was treated with ozone (1.25 g., 26 mm.) at —78°C. The resulting mixture was flushed with nitrogen. The mixture was allowed to come to 0°C. and 2.42 g. (39 mm.) of dimethyl sulfide were added and the mixture stirred at this temperature for 80 minutes. After cooling to —78°C, a suspension of 1.47 g. (39 mm.) of sodium borohydride in 20 ml. of absolute ethanol was added dropwise. The resulting mixture was allowed to come up to room temperature and then stirred for 80 minutes. The methanol was removed under vacuum to produce 3.54 g. of product (80% of theory), b.p. 72° (0.2 mm., short path distillation).

I.R. 2.90 μ(—OH), 5.75 μ(C=O).
N.M.R. 4.38 γ(2H, multiplet, olefinic),
5.02 γ(1H, heptet, J=6,

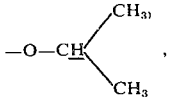

6.37 γ(2H, triplet, J=6, —C$\underline{H}_2$—O),
6.93 γ(2H, doublet, J=7, —CH$_2$—CO—),
7.68 γ(3H, multiplet, —O$\underline{H}$ —CH$_2$—),
8.80 γ(6H, doublet,

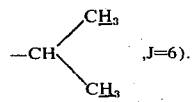

EXAMPLE XI

Isopropyl cis 6-hydroxy-3-hexenoate p-toluene sulfonate p-Toluene sulfonyl chloride (1.425 g., 7.5 mm.) was added at 0°C to a solution of 1.00 g. (5.8 mm.) of isopropyl cis 6-hydroxy-3-hexenoate in 2.37 g. of dry pyridine. The resulting mixture was stirred at 0°C for 4 hours. The crude product was poured on ice and concentrated hydrochloric acid, sodium carbonate till neutral and dried over potassium carbonate. Evaporation of the solvent produced 1.32 g. (70% of theory) of crude tosylate.

I.R. 5.80 μ(C=O), 6.26 and 6.98 μ( C=C )
N.M.R. 2.77 γ(4H, multiplet, aromatic)
4.48 γ(2H, multiplet, olefinic)
5.04 γ(1H, heptet, J=6,

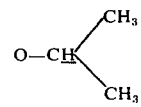

6.00 γ(2H, triplet, J=7, —C$\underline{H}_2$—O
7.05 γ(2H, doublet, J=8,

7.60 γ(3H, singlet, —C$\underline{H}_3$)
7.67 γ(2H, multiplet, —C$\underline{H}_2$—CH—)
8.82 γ(6H, doublet, J=7,

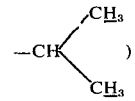

EXAMPLE XII cis 3-Hexen-1-ol

The crude isopropyl cis 6-hydroxy-3-hexenoate p-toluene sulfonate (1.00 g., 3.07 mmoles) was dissolved in 20 ml. of dry ether. To this solution was added 342 mg. (9.00 mm.) of lithium aluminum hydride in dry ether. After the addition was complete the mixture was stirred at 25°C for 1 hour. The excess lithium aluminum hydride was decomposed with first wet ether and finally water. The product was extracted with ether, dried over magnesium sulfate and the solvent evaporated. There was produced 0.26 g. (2.6 mm., 84.5% of theory) VPC was identical with authentic sample.

EXAMPLE XIII

In accordance with the procedures of Examples I–II but starting in place of anisole, with n-propoxy benzene, -n-butoxy benzene, tert.butoxy benzene, n-pentoxy benzene, cyclopentoxy benzene, cyclohexoxy benzene, cycloheptoxy benzene or diphenyl ether, there is obtained n-propyl cis-6-hydroxy-3-hexenoate
n-butyl cis-6-hydroxy-3-hexenoate
tert.butyl cis-6-hydroxy-3-hexenoate
n-pentyl cis-6-hydroxy-3-hexenoate
cyclopentyl-cis-6-hydroxy-3-hexenoate
cyclohexyl cis-6-hydroxy-3- hexenoate
cycloheptyl cis-6-hydroxy-3-henenoate
and cis-6-hydroxy-3-hexenoyl anhydride

EXAMPLE XIV

In accordance with the procedures of Examples III, but where in place of methyl cis-6-hydroxy-3-hexenoate there are utilized the products of Example XIII there are obtained the corresponding p-toluene sulfonates.

EXAMPLE XV

In accordance with the procedures of Examples III, VII, and XIV but where in place of p-toluene sulfoyl chloride, there is utilized benzene sulfonyl chloride or methyl sulfonyl chloride, there are obtained the corresponding benzene sulfonates and methane sulfonates respectively.

| JASMIN FLOWER (PERFUME COMPOSITION) | Parts |
| --- | --- |
| Undecalactone 10% | 8 |
| Nonalactone 10% | 5 |
| Methyl-phenyl glycidate ethyl ester 10% | 20 |
| Methyl anthranilate | 10 |
| Cis 3-hexenol (pure) | 4 |
| Indole 10% | 3 |
| Hydroxycitronellal | 24 |
| Cinnamic alcohol | 15 |
| Phenyl propyl alcohol | 30 |
| Cryptone | 20 |
| Dihydrojasmone | 6 |
| Peruviol Robertet | 25 |
| Essence of cardamone | 5 |
| Phenyl ethyl butyrate | 15 |
| Phenyl ethyl alcohol | 30 |
| Linalyl acetate | 50 |
| Phenyl ethyl acetate | 30 |
| Bois de rose linalool | 140 |
| Benyzl salicylate | 60 |
| Eugenyl acetate | 10 |
| Benzyl propionate | 20 |
| Benzyl acetate (pure) | 160 |
| α-Amyl cinnamaldehyde | 210 |
| Dimethyl Benzyl carbinyl acetate | 5 |
| p-Cresol (pure) | 5 |
| Nerol | 30 |
| Benzyl | 55 |
| Absolute civette 10% | 10 |

Example XVII

| Cognac Type Flavor (Flavor Composition) | |
| --- | --- |
| Furfural 1% | 50 |
| Benzaldehyde 1% | 50 |
| Cyclotene 1% | 30 |
| Palotone 1% | 10 |
| Methyl-phenyl-glycidate ethyl ester 1% | 20 |
| Paraldehyde 10% | 30 |
| Caproic acid 10% | 10 |
| Tincture of vanillin (10%) | 30 |
| Balsam of Tolu 10% | 10 |
| Isobutyl acetate | 30 |
| Cis 3-hexenol 10% | 20 |
| Enanthic ether | 40 |
| Ethyl palargonate | 30 |
| Banana (Haarman and Reimer) | 40 |

Example XVII -Continued

| Cognac Type Flavor (Flavor Composition) | |
| --- | --- |
| Ethyl Acetoacetate | 50 |
| Amyl Laurate | 10 |
| Ethyl lactate | 110 |
| Ethyl butyrate | 10 |
| Essence of the sediment of the wine of Alsace | 20 |
| Pyroligneous alcohol simple | 300 |
| Alcohol 96% | 80 |

I claim:

1. The process for the preparation of cis-3-hexen-1-ol from a phenyl ether of the formula

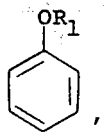

wherein $R_1$ is lower alkyl of 1–6 carbon atoms, cycloalkyl of 4–8 carbon atoms or phenyl via a sequence of reactions which comprises:

a. 1,4-hydrogenating the aromatic ring of the phenyl ether via a Birch reduction to a 1-alkoxy-1,4-cyclohexadiene of the formula

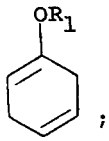

b. selectively oxidatively cleaving the alkoxy substituted 1,2 double bond of the 1-alkoxy-1,4-cyclohexadiene by reacting with an equimolar amount of ozone to provide a 6-oxo-cis-3-hexenoate of the formula

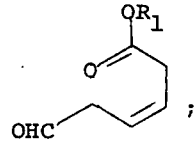

c. selectively reducing the aldehyde group of the 6-oxo-cis-3-hexenoate with sodium borohydride to form a 6-hydroxy-cis-3-hexenoate of the formula

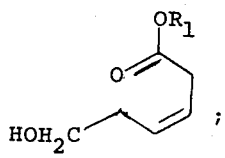

d. esterifying the alcohol group of the 6-hydroxy-cis-3-hexenoate to a 6-sulfonyloxy-cis-3-hexenoate of the formula

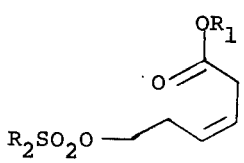

wherein $R_2$ is a lower alkyl of 1–6 carbons, a phenyl, an alkyl phenyl or a napthyl radical; and e. selectively reducing the 6-sulfonyloxy-cis-3-hexenoate with lithium aluminum hydride to form the cis-3-hexen-1-ol.

2. The process of claim 1 wherein the aromatic ring of the phenyl ether is 1,4-hydrogenated according to the Birch reduction utilizing an alkali metal chosen from the group consisting of lithium, sodium and potassium, liquid ammonia, and an alkanol to provide the 1-alkoxy-1,4-cyclohexadiene.

3. The process of claim 1 wherein the phenyl ether is converted to the 1,4-cyclohexadiene electrolytically by passing a direct electrical current through a solution of the phenyl ether and lithium chloride in methyl amine.

4. The process of claim 1 wherein reacting the phenyl ether with an alkali metal chosen from the group consisting of lithium and sodium, in ammonia, in the prsence of an alkanol thereby providing a 1-alkoxy-1,4-cyclohexadiene and then reacting with not more than an equimolar equivalent of ozone at temperatures below ambient room temperature, reducing with sodium borohydride at temperatures below ambient room temperature thereby providing the 6-hydroxy-cis-3-hexenoate, reacting the alcohol with an aromatic or aliphatic sulfonyl chloride thereby providing the 6-sulfonyloxy-cis-3-hexenoate and then reacting with lithium aluminum hydride thereby providing the cis3-hexen-1-ol.

5. The process of claim 4 wherein anisole is the phenyl ether, and p-toluenesulfonyl chloride is the sulfonyl chloride.

* * * * *

UNITED STATES PATENT OFFICE
CERTIFICATE OF CORRECTION

Patent No. 3,962,354          Dated June 8, 1976

Inventor(s) Robert T. Dahill, Jr.

It is certified that error appears in the above-identified patent and that said Letters Patent are hereby corrected as shown below:

Column 3, line 59, "IV" should read -- VI --.

Column 4, line 48, "OCH3" should read -- $OCH_3$ --.

Column 5, line 1, "OCH3" should read -- $OCH_3$ --.

Column 5, line 5, "CH2" should read -- $CH_2$ --.

Column 5, line 23, "CH2" should read -- $CH_2$ --.

Column 5, line 26, "CH3" should read -- $CH_3$ --.

Column 5, line 43, "Cis" should read -- cis --.

Column 6, line 38, "CH2" should read -- $CH_2$ --.

Column 6, line 67, "2H, multiplet" should read -- (2H, multiplet --.

Column 6, line 68, "3H, triplet" should read -- (3H, triplet --.

Column 7, line 40, "N.M.R.4.30 " should read -- N.M.R. 4.30 --.

Column 12, line 2, "prsence" should read -- presence --.

Signed and Sealed this

Seventh Day of September 1976

[SEAL]

Attest:

RUTH C. MASON  
*Attesting Officer*

C. MARSHALL DANN  
*Commissioner of Patents and Trademarks*